United States Patent
Schneider et al.

(10) Patent No.: US 10,974,017 B2
(45) Date of Patent: Apr. 13, 2021

(54) SYSTEM AND METHOD FOR SENSORY TRAINING AND ASSESSMENT

(71) Applicant: TRAINPAIN LTD, Modiin (IL)

(72) Inventors: Elan Schneider, Bronx, NY (US);
Brooks Tanner, New York, NY (US);
Laurence Nash, Zichron Yaakov (IL)

(73) Assignee: TRAINPAIN LTD, Modiin (IL)

( * ) Notice: Subject to any disclaimer, the term of this patent is extended or adjusted under 35 U.S.C. 154(b) by 178 days.

(21) Appl. No.: 16/247,462

(22) Filed: Jan. 14, 2019

(65) Prior Publication Data

US 2019/0314599 A1 Oct. 17, 2019

Related U.S. Application Data

(60) Provisional application No. 62/617,481, filed on Jan. 15, 2018.

(51) Int. Cl.
A61M 21/00 (2006.01)

(52) U.S. Cl.
CPC ..... A61M 21/00 (2013.01); *A61M 2021/0022* (2013.01); *A61M 2021/0066* (2013.01); *A61M 2021/0072* (2013.01); *A61M 2205/52* (2013.01); *A61M 2230/06* (2013.01); *A61M 2230/10* (2013.01); *A61M 2230/63* (2013.01); *A61M 2230/65* (2013.01)

(58) Field of Classification Search
CPC .......... A61M 21/00; A61M 2021/0022; A61M 2021/0055; A61M 2021/0066; A61M 2021/0072
USPC .......................................................... 600/27
See application file for complete search history.

(56) References Cited

U.S. PATENT DOCUMENTS

| | | | |
|---|---|---|---|
| 6,267,733 B1* | 7/2001 | Peterson | A61B 5/0053 600/552 |
| 2009/0151737 A1* | 6/2009 | Baxter | A61F 7/10 128/898 |
| 2015/0213724 A1* | 7/2015 | Shoshani | A61H 39/002 434/236 |
| 2015/0317910 A1* | 11/2015 | Daniels | G09B 21/00 84/485 R |

* cited by examiner

*Primary Examiner* — John P Lacyk
(74) *Attorney, Agent, or Firm* — FisherBroyles, LLP

(57) ABSTRACT

A device and method for sensory training and assessment are provided. The device includes a plurality of haptic drivers connected to a processing circuitry, wherein the plurality of haptic drivers are configured be secured to a body of a user to create vibrotactile stimuli; a feedback interface configured to receive feedback from the user in response to the vibrotactile stimuli; and a memory configured to store therein a sensory training program, wherein the sensory training program includes instructions for the haptic drivers to create the vibrotactile stimuli based on a selected sensory training program.

20 Claims, 7 Drawing Sheets

SYSTEM AND METHOD FOR SENSORY TRAINING AND ASSESSMENT

CROSS-REFERENCE TO RELATED APPLICATION

This application is related to and claims the benefit of priority to U.S. Patent Application No. 62/617,481, filed Jan. 15, 2018, which is incorporated herein by reference in its entirety.

TECHNICAL FIELD

The present disclosure relates generally to sensory training and assessment, and more specifically to a system and method for sensory training and assessment using somatosensory stimulation.

BACKGROUND

Dysfunctional sensory processing can be a debilitating issue for many individuals, and may be exhibited in a variety of ways. One common sensory dysfunction is a feeling of chronic pain. Pain can be caused by a variety of ailments and injuries, and is often categorized as either acute pain, lasting only a short period of time (e.g., less than 12 weeks), and chronic pain, lasting for a longer period of time (e.g., more than 12 weeks). Acute pain is a normal and healthy bodily response to an injury or disease, serving to warn an individual of a problematic area within the body. For example, after a bodily injury, the nerves in the injured area may become hypersensitive, creating elevated pain levels which serve to remind the individual to be cautious while the injury heals. This initial hypersensitivity should resolve itself within a number of weeks. For various medical and physiological reasons, this hypersensitivity sometimes does not resolve, and the pain remains present for an extended period, irrespective of whether the initial injury has healed or not. When pain hypersensitivity lasts longer than 12 weeks, it is categorized as "chronic pain." Chronic, or persistent, pain currently affects about 100 million adults in the U.S., making it a significant and pressing medical issue. In addition to the physically painful sensations, the effects of chronic pain are multidimensional. Many affected users can no longer effectively work, have impaired sleep schedules, or have feelings of depression or anxiety, each of which can impact social relationships and their sense of self within their social environment.

Pain, both acute and chronic, is a complex biological experience. Pain does not simply travel from the various body locations directly to the individual's brain. Rather, nerves in the various limbs and organs send electrical signals to the spinal cord, which are then modulated (i.e., amplified or inhibited), and then distributed to regions throughout the brain where the signals are further processed. Based on many factors (e.g., context, meaning, memory, competing motivations, mood, and so on), the brain may produce a small amount of pain, a large amount of pain, or no pain at all from an identical physical state.

Thus, the amount of pain felt by the individual may not be an accurate reflection of the amount of tissue damage or severity of organ injury. Rather, pain can be conceptualized as the brain's understanding of how much protection the body needs, and whether any behavior is required to restore homeostasis. It is for this reason that chronic pain can fluctuate moment to moment, and day to day, or context to context, even when there are no changes in the underlying tissues, and why the amount of pain can be very different than the amount of tissue damage (e.g., a paper cut can produce a lot of pain, while a shark bite may be painless at the moment of injury).

Pain hypersensitivity within the context of chronic pain is complex, and involves functional and structural changes at multiple locations in the nervous system (e.g., spinal cord, brainstem, prefrontal cortex, and so on), and affects multiple stages of sensory processing (e.g., detection, modulation, salience detection, valence, memory, learning and so on). The widespread and complex changes that manifest as chronic pain can be illustrated by the following examples: the brain may treat non-threatening sensory input as highly threatening, the brain's attentional system may become hypervigilant to certain types of sensory input, or the brain may excessively amplify certain types of sensory input while not sufficiently inhibiting other sensory input. The maladaptive changes in the nervous system are learned (e.g., through sensory experience), and research has shown that these changes can be unlearned through therapy and training. Treatment of acute pain (in the first weeks after an injury) is focused on the underlying injury or inflammation. After approximately 12 weeks, the treatment strategy shifts and focuses on reducing nerve hypersensitivity.

With this new knowledge about pain in general, and chronic pain specifically, there has been a shift in priorities for pain researchers and health professionals. The traditional focus has been directed to identifying the underlying tissue damage responsible for chronic pain and developing treatments that target underlying tissue damage (e.g., spine surgery, strength exercises and similar treatments directed to the pain-producing areas).

A new focus is developing that emphasizes nerve sensitivity. Researchers and clinicians examine pain system hypersensitivity, and evaluate treatments based on their effect on pain system hypersensitivity. Traditional treatments are being re-examined for their effects on pain system hypersensitivity. Such studies have focused on the effectiveness of treatments such as exercise, meditation, cognitive behavioral therapy, hypnosis, massage and medications.

It would therefore be advantageous to provide a solution for easing chronic pains that would overcome the challenges noted above.

Several prior art publications deal with similar issues as those described above, however each of them has one or more drawbacks associated therewith, and none of them describe the inventive solution of the present invention as described herein.

WO 2015028480 to Mena Benito et al. discloses a pain relieving stimulation system for relieving tinnitus or pain using stimulation. Tactile stimulation is combined simultaneously with a rhythmically aligned non-tactile (e.g., auditory, visual) stimulation. Mena Benito's tactile stimulator device may be arranged to provide at least one of: a mechanical stimulation and an electrical stimulation of a part of the person's body. The mechanical stimulation may be in the form of vibration of a part of the person's body, e.g. an arm or hand or it may be in the form of one or more pins serving to provide a pricking or dabbing of an area of the skin of the person, e.g. on the person's arm. Such types of stimulation can be implemented in a wearable battery powered device, e.g. a belt, a band, or the like, shaped so as to fit onto a specific body part, e.g. a wrist band or a back belt etc.

Mena Benito fails to describe a system that is capable of simultaneous or near simultaneous tactile stimulation at two or more areas of the body to enable the training of a user to focus attention at a particular area of the body. Furthermore, patterns of stimulation are not employed by Mena Benito's system nor are any means or methods of collecting feedback from the user, providing feedback to the user or subsequent adjustment of stimulation using user feedback.

US 20090151737 to Baxter discloses an apparatus, system and methods for reducing pain perception by focusing a user's attention on a positive stimulus. The apparatus consists of "focus cards" with graphics on one side and "indicia" on the other comprised of tasks and questions that can be directed to the user to focus the user's attention. The system can also include a thermal and/or vibratory device applied to the skin during a painful procedure to temporarily reduce pain via distraction. In an example, a child getting an injection is presented with one of a series of cards with instructions/questions that require focusing attention on the graphics of the card thereby distracting from pain. This can be combined with a thermal or vibrating analgesic device placed near the site of the pain.

Baxter provides for applying stimulation at a single body location and only at or near the expected pain site and it is used only at the time of expected perceived pain. The method does not provide for the querying of the user with respect to tactile stimulation, recording of input from the user, comparing that input to internally generated data of the system, providing feedback to the user with respect to such comparison or adjusting the types or timing of stimulus based on this comparison and other data (including subjective factors and user response data under various scenarios including scenarios involving the delivery of threat cues, as defined below).

Baxter's device describes very generally only one stimulator at only one area of the body and does not allow for varying patterns or intensities of stimulation. It would not be obvious for Baxter to use additional "vibratory means", as such an embodiment is not described in its method of use. The system does not have any interface which allows input from or feedback to the user regarding the stimulation. (The only mechanism for feedback is the questions on the backs of the cards delivered verbally by an individual.)

U.S. Pat. No. 6,267,733 to Peterson et al. discloses: computer-implemented methods and apparatus for treating motor control and somatosensory perception deficits and further, a training regime including somatosensory perception and motor control exercises which may be flexibly administered. Several training apparatus are described for implementing the somatosensory perception and motor control exercises. In one embodiment the device includes a plurality of force sensors situated in proximity such that each may receive one or more fingers from a human hand. In another embodiment the device includes a set of pins coupled with actuators wherein each pin is capable of independent vertical displacement. In another embodiment the devices includes a probe coupled with an actuator capable of linear displacement.

The device of Peterson et al. does not describe simultaneous, near simultaneous or alternating stimulation at two or more non proximate areas of the body, or stimulation at an area of the body while moving that particular body part. The device describes the use of only spatial tactile discrimination as compared to temporal discrimination as described herein (in other words, the Peterson device requires the user to distinguish points of stimulation at different locations on the body only whereas the system described herein requires the user to identify patterns at a single location or timing of stimulation across two or more locations).

WO 2007139996 to Tommerdahl discloses devices, systems, methods and computer program products for non-invasive diagnosis and screening of neurological disorders. Spatio-temporal mapping can be used between skin and the central nervous system ("CNS") to assess functional connectivity in the CNS. Stimulation drivers can be independently operated to control the movement of stimulators to achieve a variety of stimulation patterns.

The device of Tommerdahl is intended for diagnosis and screening (not therapy), primarily for the detection of neurological disease such as autism, ADHD and TBI While the device of Tommerdahl can deliver controlled somatosensory stimulation patterns, a single device cannot deliver such patterns to two or more non proximate body parts simultaneously (or even in rapid succession) since the device is designed to deliver stimulation at a single location. The device cannot be used at all at certain body locations given the need to conform to the contour of many parts of the body.

The method described in Tommerdahl does not involve simultaneous or sequential stimulation at two or more non-proximate body parts, and does not involve stimulation at both a painful and non-painful body location. Feedback is solicited from the user but this does not involve asking user to shift attention between separate body parts or to alternatingly pay attention to one body part while ignoring stimulus at another. Moreover, Tommerdahl does not provide the user with repetitive feedback for training purposes, and does not incorporate algorithms that adjust tasks based on user input regarding subjective factors such as mood, fatigue, etc.

US 20150213724 to Shoshani discloses a device that creates signals, sensible to touch, in various pre-programmed shapes to treat depression, anxiety and pain. Shoshani's device does not allow concurrent or near concurrent stimulation of two or more non proximate body parts. It allows for spatio but not temporal discrimination.

The method described by Shoshani does not require shifting attention between non-proximate body parts. To the contrary, the stimulus is to be as localised as possible. The method does not involve ignoring distracting stimulus, not does it involve delivering a stimulus at painful and non-painful body parts. No algorithms or adjustment of training for subjective factors are provided. Furthermore, Shoshani does not involve tactile discrimination in the context of prescribed body movements, body positions or other threat cues.

SUMMARY OF THE PREFERRED EMBODIMENTS

In accordance with a preferred embodiment of the present invention, a somatosensory stimulation system for training a user to focus attention toward at least one selected area of the body is disclosed. The system preferably comprises a sensory stimulation device having at least two sensory stimulators securable to different areas on the body, memory storage, a central processor and a communication transfer interface. The system further comprises an I/O device, for providing communication to the user related to the training and for receiving communication from the user related to the training.

Preferably, the sensory stimulators deliver stimuli to areas of the body and are comprised of any one or more of: haptic drivers, electric stimulators, air pressure, thermal stimulators, and mechanical dilators.

The communication transfer interface is preferably a data transmission technology for enabling data to be transferred to and from the device, and is chosen from any one or more of the following: audio/video port, WiFi transmitter and Bluetooth® transmitter.

Optionally, the system further comprises a remote server for storing user profile data, and wherein the communication transfer interface enables data transmission between the device and the remote server.

The I/O device is preferably chosen from any one or more of: a smartphone, a handheld device, a tablet computer, a personal computer, a wearable device, a display, an audio system, a keyboard, a game controller and a virtual reality system.

The I/O device communicates one or more of the following instructions to the user: focus attention toward an area of the body; focus attention away from an area of the body; ignore an area of the body; and, place the body in a certain position.

Optionally, the system further comprises a passive response device for passively receiving communication from the user related to the training. The passively received communication is preferably received from the user through the collection of physiological data via one of: brain sensor, position/movement sensor, electrodermal monitoring device and heart rate monitor means. The brain sensor is optionally an EEG device that measures alpha and gamma frequencies in the regions of the user's brain associated with areas of the body that the user is instructed to focus attention toward, and measures alpha and gamma frequencies in the regions of the user's brain associated with areas of the body that the user is instructed to ignore.

The present invention additionally preferably comprises a method of training a user to focus attention toward at least one area of the body. The method comprising the steps of:
  a. providing the somatosensory stimulation system described above;
  b. approving, via the I/O device, a selected user profile for use during the training, by one of: creating a new user profile and accessing a previously created a user profile;
  c. determining, via the I/O device, a training program for the user based on the selected user profile, the training program comprising the steps of:
    i. securing a first sensory stimulator to a first area on the body and securing a second sensory stimulator to a second area on the body;
    ii. providing the user with initial instruction on the aspects of the stimulation to attend to for the sensory discrimination task used during the training program;
    iii. activating the first sensory stimulator for a period of time and activating the second sensory stimulator for a period of time;
  d. receiving communication from the user related to the training, via at least one of:
    i. the I/O device; and,
    ii. the passive response device.

The method of the present invention preferably further comprises at least one of the following steps:
  e. updating the training program and providing the user with supplemental instructions based on the communication received from the user; and,
  f. updating the selected user profile according to the results of the training program.

In the method of the present invention, the selected user profile preferably comprises data related to at least one of: pain at at least one area of the user's body; sensory dysfunction at at least one area of the user's body; and, the user's performance during previous training.

The user profile is preferably stored in one or more of the following: internally in the memory storage of the sensory stimulation device, externally in a memory card and remotely in a server database.

The training program is optionally determined based on data associated with one or more of: pain of the user; sensory dysfunction of the user; a combination of data associated with one or more of: at least a specific area of the body of the user and an environment, wherein at least one the specific area of the body and the environment is associated with one or more of: pain of the user and sensory dysfunction of the user. Additionally, the training program is optionally determined based on at least one of: the current state of health of the user and the emotional mood of the user, each of which is determined from a pre-training interview, the results of which are updated to the selected user profile and input into the device via the I/O device.

The method of the training program is optionally also determined by one of: automatically, based on the user profile; and, manually, by one of: the user; and, a professional health provider.

The method preferably further comprises activation parameters comprising one or more of the duration, frequency, location, intensity and speed of the stimulation, and wherein the training program sets the activation parameters of each sensory stimulator.

The training program preferably sets at least one of the initial instructions and supplemental instructions to the user in combination with the activation parameters of each sensory stimulator.

Preferably, each of the first area of the body and the second area of the body in the method of the present invention is selected from one of: an area of the body associated with pain; an area of the body not associated with pain; an area of the body associated with sensory dysfunction such that sensory information is amplified above normal levels; an area of the body associated with sensory dysfunction such that sensory information is prioritized over other areas; and, an area of the body associated with sensory dysfunction such that sensory information is associated with one or more environmental contexts.

For at least one of the initial instructions and supplemental instructions, the user is preferably instructed to focus attention on one or more areas of the body including at least one of the following: the user is instructed to focus on one of the first and second area of the body and ignore sensory stimulation at the other of the first and second area of the body; the user is instructed to ignore the first and second area of the body to which the sensory stimulators are attached, and focus on a third area of the body; the user is instructed to maintain focus for a duration at more than one area of the body simultaneously; the user is instructed to focus on different areas of the body in a sequential manner; and, the user is instructed to shift focus between the first and second areas of the body along with the shift in activation of the sensory stimulators between the first and second body areas.

In the method of the present invention, the sensory stimulators are optionally activated in at least one of the following arrangement: concurrently; sequentially; and, when one sensory stimulator is activated the other is deactivated.

The communication related to the training that is preferably received from the user and optionally includes responses related to one or more of: the duration, timing and location of the stimuli.

Updating the training program optionally includes adjusting the activation parameters of each sensory stimulator.

The supplemental instructions optionally include requiring the user to adjust body positions or move the body in specific ways.

The adjusting of each sensory stimulator activation preferably includes reducing the period of time between activation of one or more of the stimulators.

Preferably, the virtual reality system is in communication with the output device, and the virtual reality system provides the user with a virtual environment to experience the training therein, such that the virtual environment triggers at least one of: pain; sensory dysfunction; an altered mood; and, an attention directing response.

Preferably, measurements from at least one of: a brain sensor, a position/movement sensor, electrodermal monitoring device and heart rate monitor means, is utilized to adjust the training program.

Optionally, the method further comprises the steps of: determining the Interbeat Stimulus Interval (ISI) threshold for painful and non-painful areas of the body; comparing and assessing the ISI data; and, adjusting the training program based on the ISI data. Preferably, the method further comprises the steps of: measuring the ISI threshold: at a single painful area of the body associated with pain; at a single area of the body associated with pain while a distracting sensory stimuli is applied to a contralateral area of the body not associated with pain; at a single area of the body not associated with pain; and, at a single area of the body not associated with pain while a distracting sensory stimuli is applied to a contralateral area of the body associated with pain. Preferably, the method further comprises the steps of: calculating the distraction delta from the measured data; comparing the distraction delta at the area of the body associated with pain with the distraction delta at the area of the body not associated with pain; and, assessing the brain function differences in processing information at the area of the body associated with pain compared with an area of the body not associated with pain.

BRIEF DESCRIPTION OF THE DRAWINGS

The foregoing and other objects, features, and advantages of the disclosed embodiments will be apparent from the following detailed description taken in conjunction with the accompanying drawings.

DETAILED DESCRIPTION OF THE PREFERRED EMBODIMENTS

Figure 1:
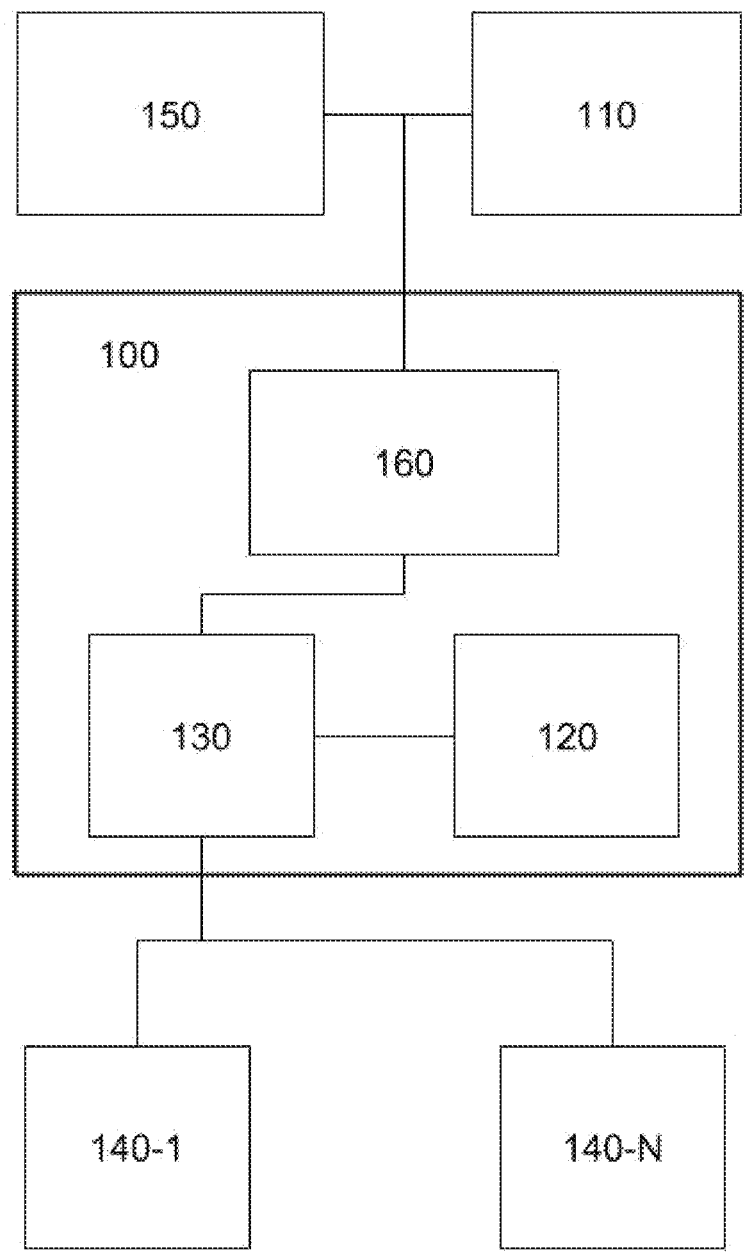
FIG. 1 is a block diagram of the system for sensory training according to a preferred embodiment of the present invention.

It is important to note that the embodiments disclosed herein are only examples of the many advantageous uses of the innovative teachings herein. In general, statements made in the specification of the present application do not necessarily limit any of the various claimed embodiments. Moreover, some statements may apply to some inventive features but not to others. In general, unless otherwise indicated, singular elements may be in plural and vice versa with no loss of generality. In the drawings, like numerals refer to like parts through several views.

The various disclosed embodiments include a system and method for sensory training using somatosensory stimulation. A preferred embodiment of the system of the present invention comprises a device having two or more sensory stimulators, connected to a processing circuitry (central processor). The sensory stimulators are configured to be secured to various areas on a user's body. Based on a sensory training program, the device is adapted to send signals to the sensory stimulators for sensory perception tasks to take place at particular areas of the body. The areas of interest may include areas exhibiting hypersensitivity, for example, increased feelings of pain, as well as areas exhibiting normal sensory function. The system is further configured to receive feedback from a user based on the training program in order to assess his performance and adjust future training programs to be more effective for that user.

FIG. 1 shows a block diagram of a first aspect of the preferred embodiment of the system of the present invention, comprising a sensory stimulation device 100 with memory storage 120, a central processor 130, a communication interface 160 and two or more sensory stimulators, such as haptic drivers 140-1 to 140-N, (hereinafter referred to individually as haptic driver 140, or in plural as haptic drivers 140, for simplicity) where N is an integer equal to or greater than 2, are connected to the central processor 130. An input/output (I/O) device (user interface) 110 and optionally, a passive response device 150, described herein below, are connected to communication interface 160 of the sensory stimulation device 100.

In this aspect, haptic drivers 140 are tactile stimulators that are configured to attach to various locations on a user's body and deliver vibrotactile stimuli thereto. For example, they may be secured to a painful or a non-painful body part of the user to trigger stimulation. As a non-limiting example, the haptic drivers 140 include a pair of coin type vibrating motors and are configured to be secured to two or more areas on an individual's body. For example, they may include an adhesive or a friction mount, such as a clip or elastic band, to be securely attached to various body parts or they may be secured with hook and loop fasteners, magnets, tape designed for use on the skin, or any suitable method of temporarily securing to the body. It is understood that the stimulation may be performed by any other suitable form of stimulation such as: electrical stimulation, air pressure, thermal stimulation, etc.

The device 100 is configured to train and/or assess a user using sensory or somatosensory stimuli, and query a user regarding their perception of the stimuli. The device delivers various patterns or configurations of stimuli that vary according to intensity, duration of discrete stimuli, number of discrete stimuli, length of intervals between stimuli, duration of patterns and the like, and the user is asked to correctly identify such patterns. In an embodiment, the haptic drivers 140 are placed on two or more areas on a user's body. The user may be informed what stimuli to expect, which to focus on and pay attention to, which to ignore, and the like.

In an embodiment, the central processor 130 is configured to send signals to the haptic drivers 140 to carry out a predetermined set of stimuli by activating the haptic drivers 140 at certain intervals. A user communicates information such as feedback via the I/O device 110. The I/O device 110 comprises one or more of: a smartphone or any other handheld device, a tablet computer, a personal computer, a wearable device, a keyboard, a game controller, a display, an audio system, and a virtual reality system, etc. Alternatively, feedback information from a user is received automatically, without the user's explicit input, via the passive response device 150, which comprises one or more sensors attached to or directed at the user's body, such as an Electroencephalogram (EEG) device, position/movement sensor, electrodermal monitoring device, heart rate monitor, etc.

The system of the present invention is configured to execute multiple different sensory training programs. As an example, a sensory training program may involve training a user to switch the focus of their attention from a first body area to a second body area using two haptic drivers, where N=2. In such a program, a first haptic driver 140-1 is attached to the first body area, and a second haptic driver 140-2 is attached to a second body area. In one version of the program, the first body area is an area where a user experiences sensory dysfunction, such as chronic pain or other hypersensitivity. It should be noted that the hypersensitivity addressed by the device is not limited to pain, and may include other aversive sensations, such as a chronic feeling of an itch at one or more body areas of a user.

As another example, the sensory training program may be configured to train the user to switch their focus from the first body area to the second body area. The training may include activating the first haptic driver 140-1 for a period of time, and then switching to activate the second haptic driver 140-2 for a period of time. The two or more haptic drivers may be active concurrently or sequentially depending on the training program. In an embodiment, the user may be instructed to anticipate the sensory switch even before the stimuli are performed by the haptic drivers 140. In an embodiment, the period of time for each stimulus may be progressively adjusted to train the user to be able to shift their focus between the first body area and the second body area as required.

Further, in an embodiment, the first body area is an area associated with pain, and the second area is an area not associated with pain, or vice versa. In a further embodiment, neither or both the first area and second area are associated with pain. An area associated with pain may include an area of the user's body where they have been experiencing sensory dysfunction such that sensory information is amplified above normal levels, or where they have been experiencing sensory dysfunction such that sensory information is prioritized over other areas, or where sensory information is associated with one or more contexts, such that certain sensations are felt or amplified when the user is in a particular environment, and the like.

As mentioned above, the user provides feedback communication by actively responding to queries generated by the I/O device 110, for instance, regarding the stimulation patterns of the device 100, thereby indicating how successful the user was in focusing on the first or second body area or in switching their attention rapidly between the areas. The queries and feedback responses may be implemented as a game or in a game-like manner, for instance, where the user must accomplish a set goal within a training program session, solve a puzzle, and the like.

As mentioned above, in a preferred embodiment, the passive response device 150 comprises an EEG device for measuring the alpha and/or gamma frequencies in different regions of the user's brain during the training program. When a high alpha frequency (low gamma frequency) is detected in a region of the brain associated with a particular area of the body, it indicates a strong sensory inhibition, and therefore lower pain perception in the corresponding area of the body. Similarly, when a low alpha frequency (high gamma frequency) is detected in a region of the brain associated with a particular area of the body, it indicates a weak sensory inhibition, and therefore a higher pain perception in the corresponding area of the body.

Whether a user exhibits high or low alpha/gamma frequencies is indicative of the user's ability to perform a sensory discrimination task well, such as following instructions to focus on one area of the body while ignoring another area of the body. If the user is capable of following these instructions, a decreased alpha activity (increased gamma activity) will be measured in the area of the brain corresponding to the area of the body that the user is meant to focus on, whereas an increase in alpha activity (decreased gamma activity) will be measured in the area of the brain corresponding to the area of the body that the user is meant to ignore.

In yet a further example of the sensory training program, the user is instructed to focus on one body area (the "targeted area") while ignoring any stimuli applied to other body areas (the "distraction area(s)"). For example, a first haptic driver 140-1 may be placed on a painful body area, and a second haptic driver 140-N may be placed on a non-painful body area. The user must focus and give feedback on the non-painful body area while ignoring all stimuli produced on the painful body area.

In yet an additional example of the somatosensory training and/or assessment program, two pulses are delivered with a short pause between them (this pause is called the Interbeat Stimulus Interval, ISI). This sequence (pulse-pause-pulse) is repeated multiple times with different ISI durations in order to determine the minimum ISI duration at which the user can clearly perceive two distinct pulses. This minimum detectable duration is the ISI discrimination threshold. The ISI discrimination threshold is measured with four different procedures: 1) at a single painful body part, 2) at a single painful part while distracting sensory stimuli is applied to a contralateral non-painful body part, 3) at a single non-painful body part, and 4) at a single non-painful part while distracting sensory stimuli is applied to a contralateral painful body part. The difference in the minimum detectable ISI when measured at a body part with and without distracting stimuli is the "distraction delta".

The distraction delta measured at the painful body part is compared to the distraction delta measured at the non-painful body part to assess brain function differences in processing information at a painful area of the body as compared to non-painful area of the body. The assessment could conclude, for instance, that in the presence of competing sensory information, the brain is better at inhibiting sensory information at one particular area of the body, as compared to inhibiting sensory information from a different particular area of the body.

This assessment process occurs prior to training or over the course of training to monitor progress and adjust the training program accordingly.

In another example of the sensory training program, the user is instructed to move certain body parts while answering queries regarding stimuli applied to either moving or stationary body parts.

In another example of the sensory training and/or assessment program, the user may be presented with certain contextual parameters or "threat cues" prior to or during delivery of stimuli. Such threat cues, which are considered to be associated with the experience of pain by the user, might include visual depictions of activities that might be considered painful, instructions to imagine certain painful movements or situations, or instructions to actually perform certain movements that might resemble movements typically associated with pain for that user.

Figure 2:
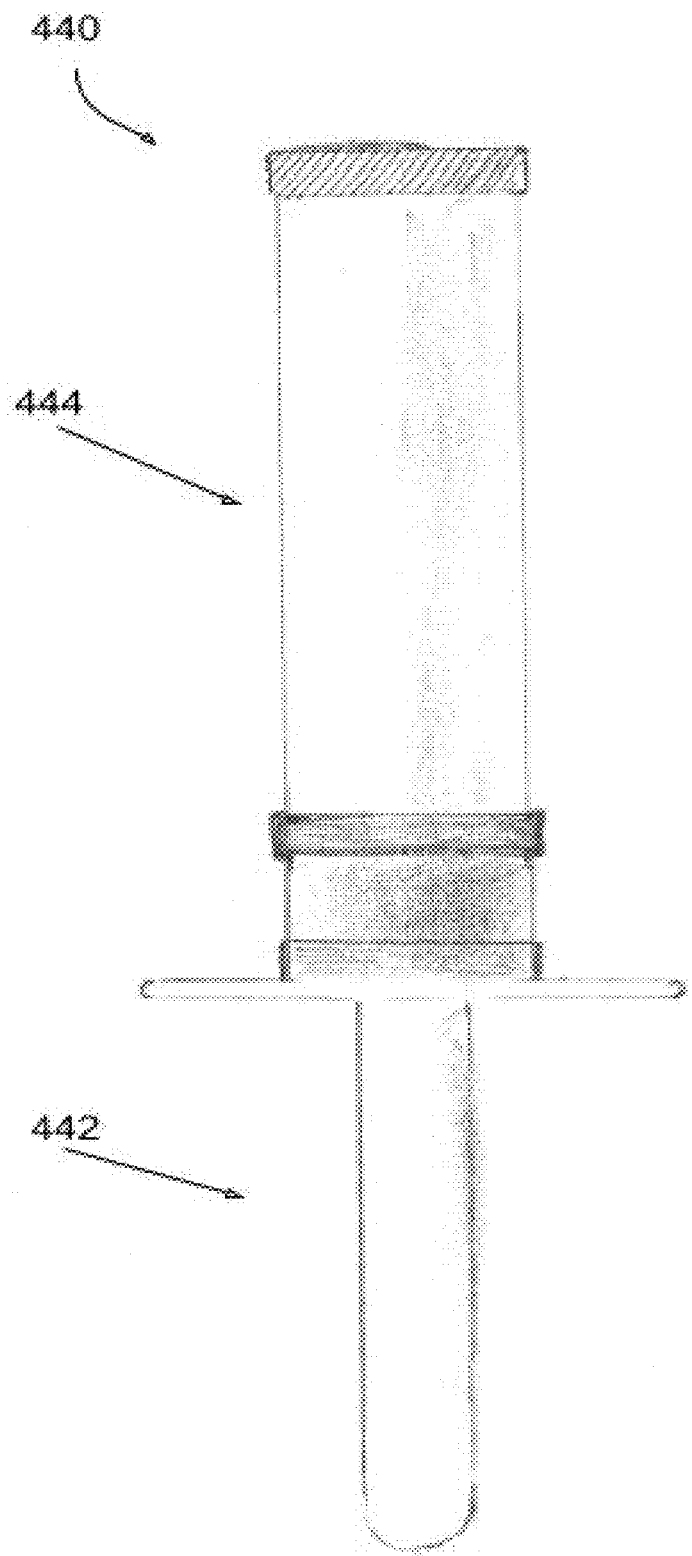
FIG. 2 is a side assembled view of a pelvic stimulator for one aspect of a preferred embodiment of the present invention.

In FIGS. 2-4 a second aspect of the preferred embodiment of the present invention is shown, wherein the device of the second aspect comprises all of the same features of the device of the first aspect of the preferred embodiment of the present invention, mutatis mutandis, with the following differences. According to the second aspect, the two or more sensory stimulators comprise at least one mechanical dilator, shown in the figures in the form of pelvic stimulator 440. FIG. 2 shows a side assembled view of pelvic stimulator 440, comprising a stimulator portion 442 and a controller portion 444 that are removably attachable to each other.

Figure 3B:
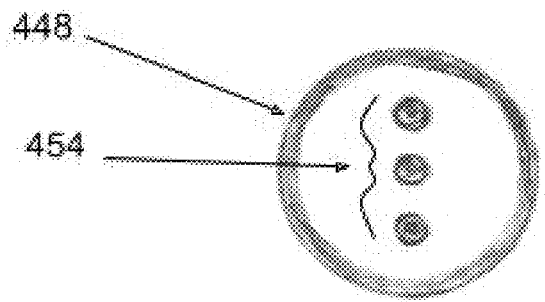
FIGS. 3a and 3b show the stimulator portion of the pelvic stimulator in aside view (FIG. 3a) and top view (FIG. 3b)
Figure 3A:
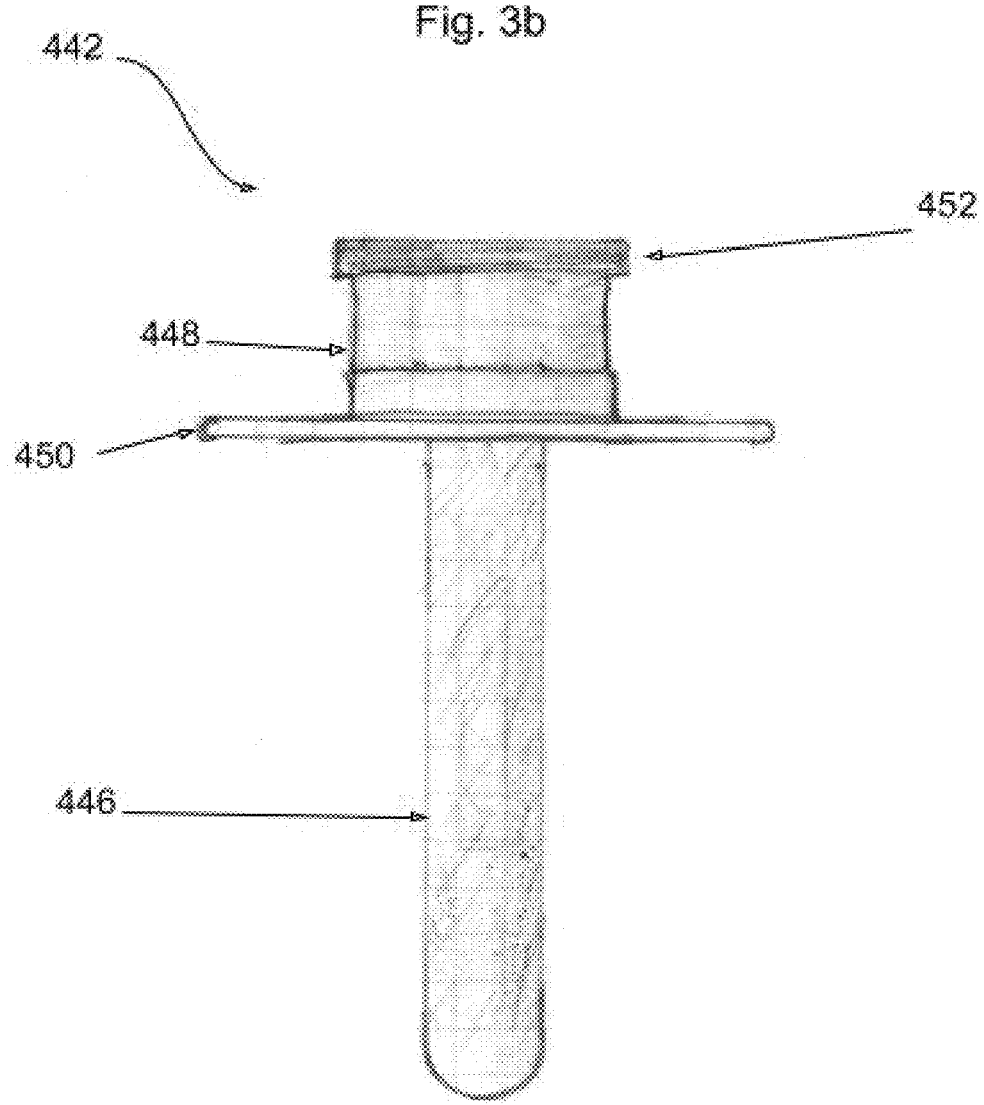

FIG. 3a shows the stimulator portion 442, comprising an insertable tube 446, and a vibration dampener 448 connected to the insertable tube 446 and separated therefrom by a partition 450. The circumference of insertable tube 446 is minimally 12.5 mm in diameter and 70 mm in length but can typically range from 12.5 mm/70 mm to 38 mm/155 mm (diameter/length). However, in one preferred embodiment (not shown), the circumference can be dilated to different sizes (e.g. via air inflation/deflation), and sensory discrimination tasks involve detecting the amount/degree of dilation. The proximal edge 452 of the wall of the vibration dampener 448 is threaded internally for joining with the controller portion 444 of FIG. 2.

Figure 4C:
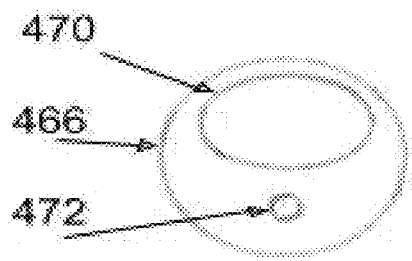
FIGS. 4a, 4b and 4c show the controller portion of the pelvic stimulator in a partially cut side view (FIG. 4a), bottom view (FIG. 4b) and top view (FIG. 4c).
Figure 4A:
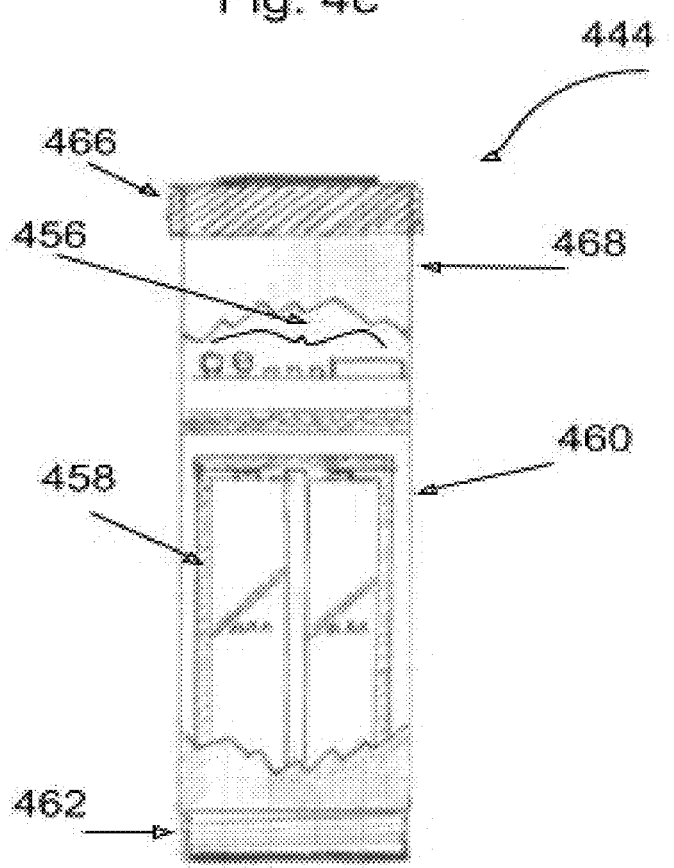
Figure 4B:
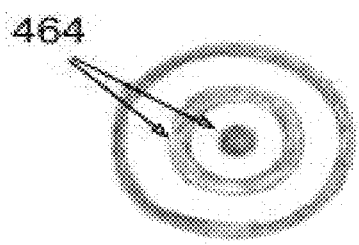

Referring to FIG. 3b, a top view of the vibration dampener 448 is shown, wherein the exposed face of the vibration dampener 448 comprises connectors 454 for connecting with corresponding contact pads (not shown in this figure) of the controller portion (see FIG. 4b).

A partially cut away side view of a preferred embodiment of the controller portion 444 is shown in FIG. 4a, exposing the internal circuitry 456 and battery pack 458 within a housing 460. The distal edge 462 of the housing 460 is threaded externally for joining with the stimulator portion 442.

Referring to FIG. 4b, a bottom view of the controller portion 444 is shown, wherein the exposed face of the controller portion 444 comprises contact pads 464 for connecting with corresponding connectors (see FIG. 3b) of the stimulator portion 442 as mentioned above.

A cap 466 is situated at the proximal end 468 of the controller portion 444 for providing a water-tight sealing of the housing 460, and shown in a top view in FIG. 4c. An on/off switch 470 for activating and deactivating the pelvic stimulator 440 is shown with an LED indicator 472 for indicating the on/off state of the pelvic stimulator 440.

Further reference herein to the components of the first aspect of the device 100 are to be understood as equally applicable to the second aspect of the present invention in which the pelvic stimulator 440 is one of the sensory stimulators.

Sensory training performed through repetition without any contextual parameters or cues is referred to as non-associative training, and may be accomplished using the disclosed system by means of executing the various aforementioned sensory training programs. Sensory training connected to contextual parameters or involving creating new associations between unrelated cues is referred to as associative training, and is discussed further below.

In operation, the stimulation is initially applied according to the training program selected via the I/O device 110. The I/O device 110 prompts the user to pay attention to a certain part of the body. The prompts are determined based on the program (initial or adjusted) currently being performed.

Typically, the sensory training program is adjusted based on feedback received via the I/O device 110 and passive response device 150 in order to more effectively implement the program for that specific user. The feedback may include at least one of: responses related to the parameters of the stimulations (e.g., intensity, speed, and duration); responses related to the nature of the interaction between a targeted area and a distraction area (e.g., relative intensity of stimulus or temporal or spatial proximity); factors requiring the shifting of attention between stimuli (e.g., the speed with which the user is required to shift their attention between painful and non-painful body parts); the type and intensity of pain (or, threat) cues, and the like. In one example, the results from EEG measurements are taken into account for determining which sensory discrimination tasks can lead to optimal alpha/gamma frequency responses in the user's brain. Similarly, alternative brain sensors (e.g. cerebral blood flow, etc.) can be used to measure neural oscillations in any other frequency (e.g. beta, delta, theta, etc.) The feedback is entered into the device 100 and saved within the memory 120.

As a further example of a sensory training program, the period of time between each stimulus is progressively reduced, such that a user is trained to shift their attention between body areas more quickly and deliberately. Feedback from the user may be received to determine the effectiveness of a training program session.

In some embodiments, the program may be configured to increase or adjust certain parameters over a period of time. For example, the program may initially require a user to first move through a range of motion, e.g. flex his spine. As time goes on, the program, based on feedback from the user, may be adjusted to increase the amount of movement required of the user.

As a non-limiting example, as mentioned above, the I/O device 110 is connected to a virtual reality (VR) system (not shown), where, for instance, a handheld device or display is embedded within a headset that can be worn by a user. The VR system may further include an audio system, such as speaker or headphone to relay instructions to the user. The audio system may include a microphone and speakers.

In a preferred embodiment, a communication interface 160 is configured to relay information from the device 100 to the I/O device 110. The communication interface 160 may include a wired interface and a wireless interface, such as, but not limited to, an audio/video port, e.g., an HDMI port, a WiFi transmitter and a Bluetooth® transmitter, and the like.

Further, the device 100 may connect to a remote server (not shown) via the communication interface 160 in order to upload and access data there from. Data may include a user profile, a plurality (library) of user profiles, statistical information based on user profiles, and the like. A user profile may include data related to a user's pain and treatment history and feedback collected from previous sensory training session, including such training data as graded movement and/or graded environment experiences that are used for a particular user.

According to some configurations, when the device 100 is equipped with a VR system, as mentioned above, the device 100 allows for an all-immersive experience for a user during the sensory training session. The display of a VR headset is configured to be mounted or worn in close proximity to a user's eyes to give the impression of experiencing a scene in first person. The VR system includes a position sensor (not shown) configured to detect the position, motion, acceleration, and the like, of a user while wearing the VR headset. For example, when a user is wearing a VR headset and turns or tilts their head, the VR system interprets a movement such as gazing to the left, and changes the displayed scene accordingly. This ensures an immersive experience for the user.

In another configuration, the I/O device 110 is a smartphone, which includes a native position sensor, such as an accelerometer. The smartphone may be mounted as a pair of goggles, for example as provided by Google® Cardboard, Samsung® Gear VR, or other VR smartphone mounts.

The device 100, including a configuration with a VR headset, allows for sensory training related to context-specific sensory processing. For example, if a user experienced a sensory dysfunction in a particular environment, the VR headset can allow the device 100 to recreate the environment in order to conduct a sensory training session within a virtual version of the relevant context. As a non-limiting example, if a user reacts with a painful sensation in their lower back when they are in a warehouse environment due to a work-related injury, the VR headset can display a virtual version of the warehouse, allowing the device 100 to employ training technique, e.g., the sensory training programs discussed above, while the user is experiencing the triggering context. As another non-limiting example, if a user experiences sensory dysfunction during a specific movement, e.g., an arm pain while turning their head to the left, the device can instruct the user to make calibrated similar movements, and a motion sensor, e.g., the sensor within the VR headset, can detect and relay such a movement to the central processor 130.

The sensory training program, disclosed herein, can be configured to be implemented in a variety of ways. For example, with the use of a VR headset, the sensory training program may present a mood altering experience, such as relaxing experience, including calming music and visuals, while a user is training. Alternatively, the sensory training program may present a pain triggering experience, such as the aforementioned warehouse example. Further, if a user experiences lower back pain when confronted with a certain context where a specific body movement occurs, such as in a warehouse, the device 100, e.g., via a display or an auditory system connected to the device, such as through the VR headset or a comparable system, may display a picture or video of another person making that same body movement, in order to acclimate and train the user within the context.

According to some exemplary embodiments, the central processor 130 may be realized as one or more hardware logic components and circuits. For example, and without limitation, illustrative types of hardware logic components that can be used include field programmable gate arrays (FPGAs), application-specific integrated circuits (ASICs), application-specific standard products (ASSPs), system-on-a-chip systems (SOCs), general-purpose microprocessors, microcontrollers, digital signal processors (DSPs), and the like, or any other hardware logic components that can perform calculations or other manipulations of information.

The memory 120 may be volatile (e.g., RAM, etc.), non-volatile (e.g., ROM, flash memory, etc.), or a combination thereof. The memory 120 is further configured to store software. Software shall be construed broadly to mean any type of instructions, whether referred to as software, firmware, middleware, microcode, hardware description language, or otherwise. Instructions may include code (e.g., in source code format, binary code format, executable code format, or any other suitable format of code). The instructions cause the central processor 130 to perform the various processes described herein. Specifically, the instructions, when executed, cause the central processor 130 to activate the haptic drivers 140 such that a specific pattern or series of sensory stimuli are executed on a user according to a sensory training program.

Figure 5:
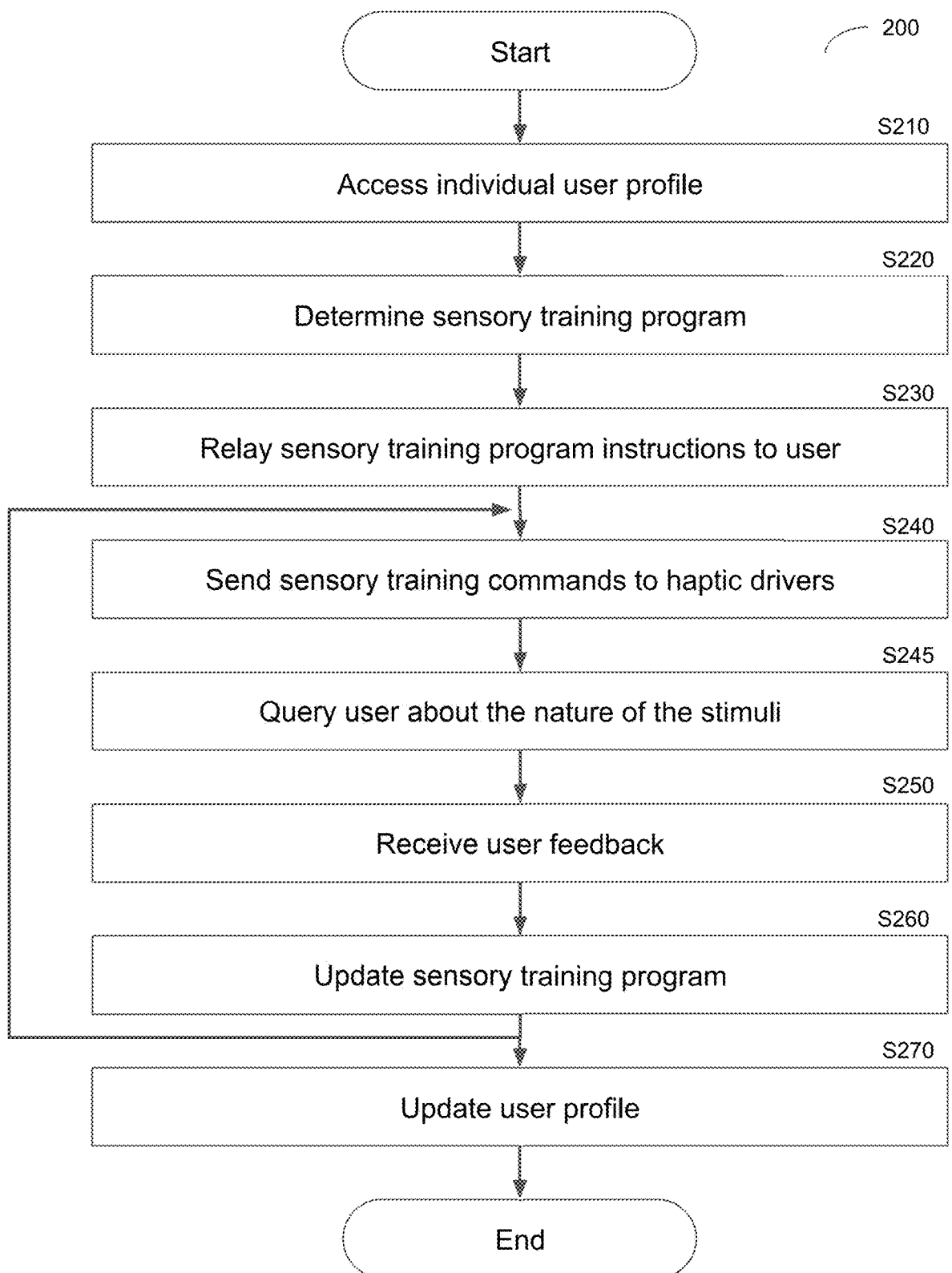
FIG. 5 is a flowchart of a method of implementing a user-specific sensory training according to an embodiment of the present invention.

FIG. 5 is a flowchart of a method 200 of implementing a user-specific sensory training according to an embodiment. At S210, a user profile is accessed. For example, the user profile may be accessed by a server requesting information from a remote database of user profiles. The user profile includes data related to chronic pain experienced by the user, sensory dysfunctions, the progress or lack thereof regarding sensory training over a period of time, VR modules and smartphone applications for chronic pain management tailored to the specific user, and so on. VR modules and smartphone apps include games and applications related to sensory training that may be displayed on a VR system or smartphone display. For example, the VR modules include pain related contexts such as images, sounds, movements, etc., related to the users experience of pain.

User profiles may further include data related to user performance from previous sensory training sessions. Reliance on measurable objective performances of the user (e.g. accuracy and response time), and subjective inputs from the user (e.g., qualitative and quantitative data such as pain scale, mood, fear, etc.) before and after the sensory training sessions may be saved to the user profile.

At S220, a sensory training program is determined. Various sensory training programs may each be designed to focus on a specific goal for the user. The sensory training program may be determined based on the user profile, or based on a manual selection, e.g., a selection input from the user or a treating therapist. Sensory training programs include, but are not limited to, programs for training users to switch focus between a first body area and a second body area, programs for training users to quickly focus on one specific body area, programs for focusing on one particular body area while disregarding distracting stimuli applied to another body area, programs for focusing on multiple body areas simultaneously, and the like, as described above with regards to FIG. 1.

At S230, sensory training program instructions are relayed to the user (patient) based on the determined sensory training program. For example, if the sensory training program is configured to apply stimuli to a painful body area and a non-painful body area, e.g., via haptic drivers 140 of FIG. 1, in order to train a user to focus on both areas simultaneously, instructions to focus on both the painful and the non-painful areas are relayed to the user. This enables a user to mentally prepare for the stimuli, as well as train their reaction to anticipated stimuli.

At S240, sensory training commands based on the determined sensory training program are sent to sensory stimulators, e.g., the haptic drivers 140 of FIG. 1. In an embodiment, the sensory training commands also include commands related to the I/O device 110 of FIG. 1. The sensory training commands cause the generation of the vibrotactile stimuli at a painful and a non-painful body part concurrently or sequentially. The stimuli can be applied in a relaxing or pain triggering mode or context. In the relaxing mode, relaxing or user chosen music can be played in the background via the I/O device 110 during the sensory training tasks.

In the pain triggering mode, the user is prompted, via the I/O device 110, to perform a physical movement that is painful prior, or simultaneously, to when the vibrotactile stimuli is applied. To this end, a picture or video or other type of cue or movement that reminds the user of their pain or which can trigger their pain is applied prior or during the sensory task. For example, a cue could be a picture of someone bending their back, or a picture of a warehouse where the user tends to have their pain attacks. The picture or video can be displayed on a VR headset or a display as discussed above.

At S245, the user is queried about the about the nature of the stimuli, for the example, the duration, timing, and location of the stimuli. In an embodiment, the query may be communicated to the user via the I/O device 110. For example, the queries can be heard via the audio system, display on the display, and so on.

At S250, the feedback from the user is received and analyzed. The feedback includes the reactions of the user to the various programs, user self-assessments regarding pain levels, responses to stimuli, and the like. In an embodiment, the feedback is received via the I/O device 110 and analyzed by the device. For example, the feedback may be received through the microphone while the analysis is performed using voice recognition. In yet another embodiment, when the user types his/her feedback, the analysis of the feedback may be based on the textual analysis. In yet another embodiment, the feedback is received from the VR headset via a visual pointer maneuvered across the screen by moving the user's head.

At S260, the sensory training program is updated based on the feedback. As a result, execution may return to S240 where new sensory training commands are generated. In an embodiment, parameters used for determining the sensory training program instructions are automatically determined and the program is updated in real-time. Further, the parameters may be adjusted based on the feedback received from a user. Parameters that may be adjusted include the speed of a stimulation task (i.e., pre-stimulus cue time), the complexity of a stimulation pattern, the intensity of a stimulation, the intensity of a distraction, the onset timing of a target stimulation, the onset timing of a distraction stimulation, the degree of similarity of a target and distraction stimulation, the onset timing difference between stimulations, and the like.

In a further embodiment, the parameters may include changes or adjustments in the environment, e.g., the environment shown via a VR system. These environment parameters may include changes in images displayed, such as completing a sensory task while watching a person lift a light box or while watching someone lift a heavy box; completing a sensory task while watching someone smiling or while watching someone grimacing; completing a sensory task while moving the neck minimally so as not to cause pain or while moving the neck further into a usually painful position; completing a sensory task while hearing "happy music" or while hearing "suspenseful music," and the like.

In an embodiment, the adjustments to the user profile take into account day to day changes in symptoms and overall trends determined from a user. For example, a user may be making good progress, and the sensory training programs are adjusted to become increasingly more challenging. When the user has a pain flare up, a day with bad mood, or night of poor sleep, the method takes this into account by receiving inputs based on, for example, a daily pre-training interview, and adjusts that day's program to be easier and to use therapy modules that the user has previously indicated that they find more pleasant. Once the flare up or poor mood has resolved (e.g., on a subsequent training day), the method may return to the overall sensory goals, and resume the trajectory of therapy program that had been abandoned during the flare up.

At optional S270, once the training session is over, the user profile is updated based on the received feedback. The updated profile may represent any progress or regression a user has had with regards to a sensory training program, and may be used to determine sensory training programs for future uses. In an embodiment, the updated profile is uploaded to a remote server for storage and future access.

The method may additionally implement machine learning to determine the ideal sensory training program for the user. In an embodiment, the profiles of multiple users are analyzed and compared to the current user. For example, a group of users (e.g., 'Type A') may fit a profile of similar sensory dysfunction, or similar pain related cues, while a different group of users ('Type B') have a different profile, and tend to experience a different set of sensory dysfunctions or pain related cues. Once these profiles are learned, e.g., by a device 100 implementing the method 200, when a future user first engages the method, the device can quickly recognize his 'type' of user profile, and be able to make rapid adjustments in the therapy protocol and sensory training programs to maximize the chances of success according to what is known about prior users who fit that profile.

Figure 6A:
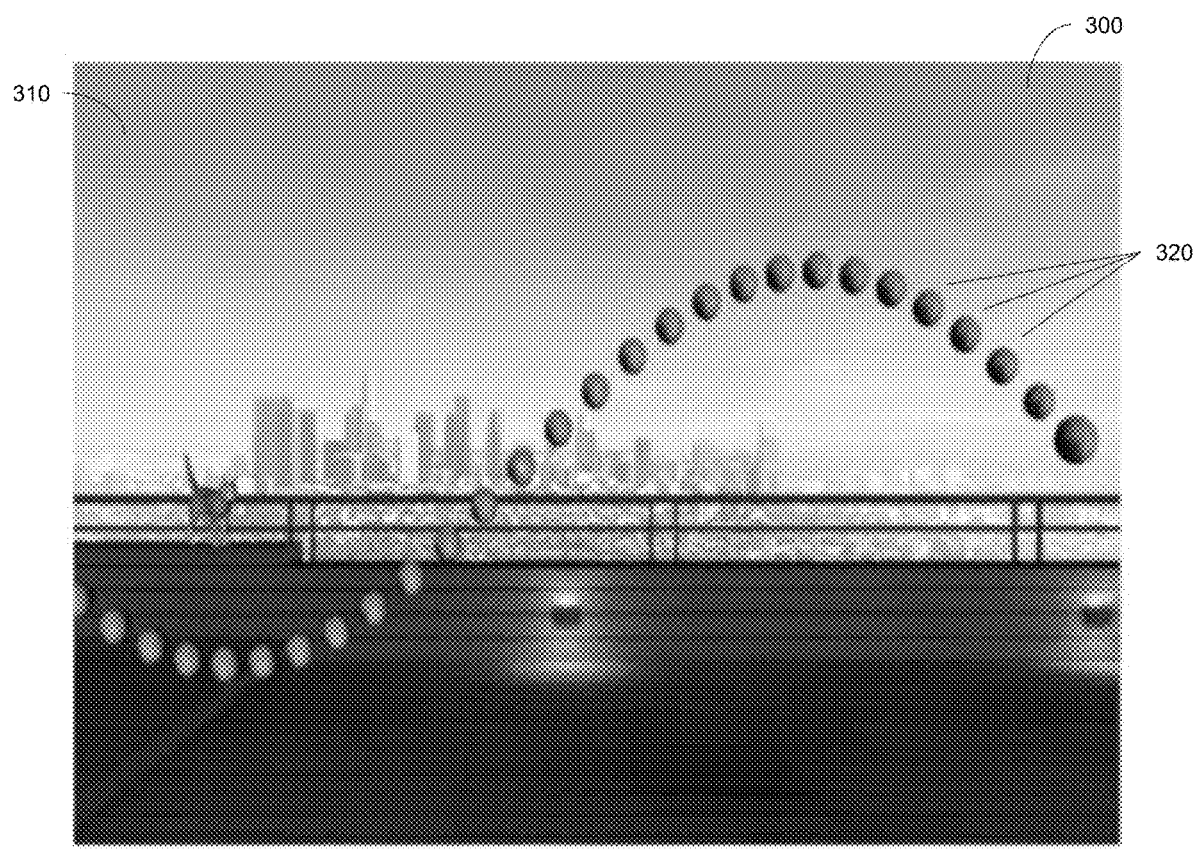
FIG. 6a is an example screenshot of a game for a virtual reality system for sensory training according to an embodiment of the present invention.
Figure 6B:
FIG. 6b is an alternative example screenshot of a game for a virtual reality system for sensory training according to an embodiment of the present invention.

FIGS. 6a and 6b are example screenshots 300 of a game implemented by the device 100 according to an exemplary embodiment. As shown in the screenshot 300 in FIG. 6a, a scene 310 is presented to a user, e.g., via a VR system by displaying the scene 310 through a VR headset. In the depicted embodiment, a game scene is shown which includes a plurality of spheres 320 arranged according to a predefined pattern. In an embodiment, the user is instructed to direct a VR pointer, e.g., a pointer linked to where the user's gaze is directed to, toward the displayed spheres 320. A sphere 320 is configured to "pop" when a user gazes at it, and triggers a stimulation, e.g., a vibrotactile stimulus via one or more haptic drivers 140 of FIG. 1. Depending on the sensory training program being executed for that particular user, the "popping" of the spheres 320 may trigger a stimulation on a painful body area, a non-painful body area, or both.

In FIG. 6b, a reward scene 330 is shown, where a number of stimuli 340 felt by the user is displayed. The number may be selected directly by a user to verify that the correct number of stimulations were felt. If the correct number 340 is selected, a congratulatory display, such as a fireworks animation, may be shown. Displaying a concrete number can be helpful in assisting and encouraging a user in their pain management training. Additionally, the celebratory imagery, such as fireworks, create a sense of accomplishment for the user.

The various embodiments disclosed herein can be implemented as hardware, firmware, software, or any combination thereof. Moreover, the software is preferably implemented as an application program tangibly embodied on a program storage unit or computer readable medium consisting of parts, or of certain devices and/or a combination of devices. The application program may be uploaded to, and executed by, a machine comprising any suitable architecture. Preferably, the machine is implemented on a computer platform having hardware such as one or more central processing units ("CPUs"), a memory, and input/output interfaces. The computer platform may also include an operating system and microinstruction code. The various processes and functions described herein may be either part of the microinstruction code or part of the application program, or any combination thereof, which may be executed by a CPU, whether or not such a computer or processor is explicitly shown. In addition, various other peripheral units may be connected to the computer platform such as an additional data storage unit and a printing unit. Furthermore, a non-transitory computer readable medium is any computer readable medium except for a transitory propagating signal.

As used herein, the phrase "at least one of" followed by a listing of items means that any of the listed items can be utilized individually, or any combination of two or more of the listed items can be utilized. For example, if a system is described as including "at least one of A, B, and C," the system can include A alone; B alone; C alone; A and B in combination; B and C in combination; A and C in combination; or A, B, and C in combination.

All examples and conditional language recited herein are intended for pedagogical purposes to aid the reader in understanding the principles of the disclosed embodiment and the concepts contributed by the inventor to furthering the art, and are to be construed as being without limitation to such specifically recited examples and conditions. Moreover, all statements herein reciting principles, aspects, and embodiments of the disclosed embodiments, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

The invention claimed is:

1. A somatosensory stimulation system for training a user to focus attention toward at least one selected area of the body, said system comprising:
   a. a sensory stimulation device having at least two sensory stimulators securable to different areas on said body, memory storage, a central processor and a communication transfer interface; and,
   b. an I/O device, for providing communication to said user related to said training and for receiving communication from said user related to said training.

2. The system of claim 1, wherein the sensory stimulators deliver stimuli to areas of the body and are comprised of any one or more of: haptic drivers, electric stimulators, air pressure, thermal stimulators, and mechanical dilators.

3. The system of claim 1, wherein the I/O device communicates one or more of the following instructions to the user:
   a. focus attention toward an area of the body;
   b. focus attention away from an area of the body;
   c. ignore an area of the body; and,
   d. place the body in a certain position.

4. The system of claim 1, further comprising a passive response device for passively receiving communication from the user related to the training.

5. The system of claim 4, wherein the passively received communication is received from the user through the collection of physiological data via one of: a brain sensor, a position/movement sensor, an electrodermal monitoring device and heart rate monitor means.

6. The system of claim 5, wherein the brain sensor is an EEG device that measures alpha and gamma frequencies in the regions of the user's brain associated with areas of the body that said user is instructed to focus attention toward, and measures alpha and gamma frequencies in the regions of the user's brain associated with areas of the body that said user is instructed to ignore.

7. A method of training a user to focus attention toward at least one area of the body, said method comprising the steps of:
   a. providing a somatosensory stimulation system for training a user to focus attention toward at least one selected area of the body, said system comprising:
      (i) a sensory stimulation device having at least two sensory stimulators securable to different areas on said body, memory storage, a central processor and a communication transfer interface; and,
      (ii) an I/O device, for providing communication to said user related to said training and for receiving communication from said user related to said training;
   b. approving, via the I/O device, a selected user profile for use during the training, by one of: creating a new user profile and accessing a previously created a user profile;
   c. determining, via the I/O device, a training program for the user based on said selected user profile, said training program comprising the steps of:
      i. securing a first sensory stimulator to a first area on said body and securing a second sensory stimulator to a second area on said body;
      ii. providing the user with initial instruction on the aspects of the stimulation to attend to for the sensory discrimination task used during the training program;
      iii. activating said first sensory stimulator for a period of time and activating said second sensory stimulator for a period of time;
   d. receiving communication from the user related to said training, via at least one of:
      i. the I/O device; and,
      ii. the passive response device.

8. The method of claim 7, further comprising at least one of the following steps:
   a. updating said training program and providing said user with supplemental instructions based on the communication received from the user; and,
   b. updating said selected user profile according to the results of the training program.

9. The method of claim 7, wherein the selected user profile comprises data related to at least one of:
   a. pain at at least one area of the user's body;
   b. sensory dysfunction at at least one area of the user's body; and
   c. the user's performance during previous training.

10. The method of claim 7, wherein the user profile is stored in one or more of the following: internally in the memory storage of the sensory stimulation device, externally in a memory card and remotely in a server database.

11. The method of claim 7, wherein the training program is determined based on data associated with one or more of:
  a. pain of the user;
  b. sensory dysfunction of the user;
  c. a combination of data associated with one or more of:
    i. at least a specific area of the body of the user and an environment, wherein at least one said specific area of the body and said environment is associated with one or more of: pain of the user and sensory dysfunction of the user;
  d. at least one of: the current state of health of the user and the emotional mood of the user, each of which is determined from a pre-training interview, the results of which are updated to the selected user profile and input into the device via the I/O device.

12. The method of claim 7, wherein the training program is determined by one of:
  a. automatically, based on the user profile; and,
  b. manually, by one of:
    i. the user; and,
    ii. a professional health provider.

13. The method of claim 8, further comprising activation parameters comprising one or more of the duration, frequency, location, intensity and speed of the stimulation, and wherein the training program sets the activation parameters of each sensory stimulator.

14. The method of claim 13, wherein the training program sets at least one of the initial instructions and supplemental instructions to the user in combination with the activation parameters of each sensory stimulator.

15. The method of claim 7, wherein each of the first area of the body and the second area of the body is selected from one of:
  a. an area of the body associated with pain;
  b. an area of the body not associated with pain;
  c. an area of the body associated with sensory dysfunction such that sensory information is amplified above normal levels;
  d. an area of the body associated with sensory dysfunction such that sensory information is prioritized over other areas; and
  e. an area of the body associated with sensory dysfunction such that sensory information is associated with one or more environmental contexts.

16. The method of claim 8, wherein for at least one of the initial instructions and supplemental instructions, the user is instructed to focus attention on one or more areas of the body including at least one of the following:
  a. the user is instructed to focus on one of the first and second area of the body and ignore sensory stimulation at the other of the first and second area of the body;
  b. the user is instructed to ignore the first and second area of the body to which the sensory stimulators are attached, and focus on a third area of the body;
  c. the user is instructed to maintain focus for a duration at more than one area of the body simultaneously;
  d. the user is instructed to focus on different areas of the body in a sequential manner; and,
  e. the user is instructed to shift focus between the first and second areas of the body along with the shift in activation of the sensory stimulators between the first and second body areas.

17. The method of claim 7, wherein the sensory stimulators are activated in at least one of the following arrangement: concurrently; sequentially; and, when one sensory stimulator is activated the other is deactivated.

18. The method of claim 7, wherein the virtual reality system is in communication with the output device, and wherein said virtual reality system provides the user with a virtual environment to experience the training therein, such that said virtual environment triggers at least one of:
  a. pain;
  b. sensory dysfunction;
  c. an altered mood; and,
  d. an attention directing response.

19. The method of claim 7, further comprising the steps of:
  a. determining the Interbeat Stimulus Interval (ISI) threshold for painful and non-painful areas of the body;
  b. comparing and assessing the ISI data; and,
  c. adjusting the training program based on said ISI data.

20. The method of claim 19, further comprising the steps of:
  a. measuring the ISI threshold:
    i. at a single painful area of the body associated with pain;
    ii. at a single area of the body associated with pain while a distracting sensory stimuli is applied to a contralateral area of the body not associated with pain;
    iii. at a single area of the body not associated with pain; and,
    iv. at a single area of the body not associated with pain while a distracting sensory stimuli is applied to a contralateral area of the body associated with pain;
  b. calculating the distraction delta from the measured data;
  c. comparing the distraction delta at the area of the body associated with pain with the distraction delta at the area of the body not associated with pain; and,
  d. assessing the brain function differences in processing information at the area of the body associated with pain compared with an area of the body not associated with pain.

* * * * *